United States Patent

Korf et al.

[11] Patent Number: 6,013,029
[45] Date of Patent: *Jan. 11, 2000

[54] MONITORING THE CONCENTRATION OF A SUBSTANCE OR A GROUP OF SUBSTANCES IN A BODY FLUID

[76] Inventors: Jakob Korf, Houtwallen 11, Vries, Netherlands, 9481 ER; Thomas Henricus Marie Terwee, Klimop 12, Roden, Netherlands, 9301 PK

[*] Notice: This patent issued on a continued prosecution application filed under 37 CFR 1.53(d), and is subject to the twenty year patent term provisions of 35 U.S.C. 154(a)(2).

[21] Appl. No.: 08/624,586

[22] PCT Filed: Oct. 10, 1994

[86] PCT No.: PCT/NL94/00248

§ 371 Date: Jun. 6, 1996

§ 102(e) Date: Jun. 6, 1996

[87] PCT Pub. No.: WO95/10221

PCT Pub. Date: Apr. 20, 1995

[30] Foreign Application Priority Data

Oct. 9, 1993 [GB] United Kingdom .................. 9320850

[51] Int. Cl.[7] ...................................................... A61B 5/00
[52] U.S. Cl. ........................ 600/363; 600/365; 600/366; 600/345
[58] Field of Search ..................................... 128/630, 632, 128/637, 760, 768, 769, 642; 604/27, 30, 35, 50, 52, 53, 93; 600/300, 309, 345, 346, 347, 573, 581, 582, 363–365

[56] References Cited

U.S. PATENT DOCUMENTS

| 4,401,122 | 8/1983 | Clark . | |
|---|---|---|---|
| 4,756,884 | 7/1988 | Hillman . | |
| 4,832,034 | 5/1989 | Pizziconi et al. | 128/632 |
| 4,919,141 | 4/1990 | Zier et al. | 128/635 |
| 5,050,604 | 9/1991 | Reshef et al. | 128/632 |
| 5,096,669 | 3/1992 | Lauks . | |
| 5,174,291 | 12/1992 | Schoonen et al. | 128/632 |

FOREIGN PATENT DOCUMENTS

| 0 125 139 | 11/1984 | European Pat. Off. . |
|---|---|---|
| 0 275 390 | 7/1988 | European Pat. Off. . |
| 0 401 179 | 12/1990 | European Pat. Off. . |
| 0183351 | 6/1996 | European Pat. Off. . |
| 28 17 617 A 1 | 4/1978 | Germany . |
| 2 208 324 | 3/1989 | United Kingdom . |
| 2 259 771 | 3/1993 | United Kingdom . |
| WO89/02720 | 4/1989 | WIPO . |
| WO90/14791 | 12/1990 | WIPO . |
| WO91/16416 | 10/1991 | WIPO . |
| WO93/20745 | 10/1993 | WIPO . |

OTHER PUBLICATIONS

Flentge et al., "An Enzyme–Reactor for Electrochemical Monitoring of Choline, etc." Anal. Biochem., vol. 204, No. 2, Jan. 1992, pp. 305–310.

Ranade, Vasant V, Drug Delivery Systems 4. Implants in Drug Delivery, Journal Clinical Pharmacol, 1990 30:871–889.

Bungay, Peter J., et al., Steady–State Theory for Quantitative Microdialysis of Solutes and Water in Vivo and in Vitro, Life Sciences vol. 46, pp. 105–119, 1989.

(List continued on next page.)

*Primary Examiner*—Linda C. M. Dvorak
*Assistant Examiner*—Bryan K. Yarnell
*Attorney, Agent, or Firm*—Varnum, Riddering, Schmidt & Howlett LLP

[57] ABSTRACT

The concentration of a substance or group of substances in a body fluid is monitored by means of an interface held in contact with a living human or animal body and a detector is positioned downstream from the interface. A profusion fluid is passed from the interface to and along the detector at a flow rate of less than 60 $\mu$l/hour. A constant flow is maintained at the low flow rate with very little or no supply of energy, allowing for a compact construction and reduced measurement delay.

54 Claims, 7 Drawing Sheets

OTHER PUBLICATIONS

J. Bolinder, U. Ungerstedt and P. Arner, "Microdialysis Measurement of the Absolute Glucose Concentration in Subcutaneous Adipose Tissue Allowing Glucose Monitoring in Diabetic Patients," Diabetologia, Springer–Verlag 1992.

U. Ungerstedt, "Microdialysis—Principles and Applications for Studies in Animals and Man," Journal of Internal Medicine, 1991:230:365–373.

Ash et al., "Subcutaneous Capillary Filtrate Collector for Measurement of Blood Glucose", Asio Transactions, vol. 38, No. 3, Jul. 1992, pp. 416–420.

De Boer et al., "Continuous Monitoring of Glucose With a Transcutaneous Microdialysis Probe", The Lancet, vol. 340, Aug. 1992, pp. 547–548.

MONITORING THE CONCENTRATION OF A SUBSTANCE OR A GROUP OF SUBSTANCES IN A BODY FLUID

BACKGROUND OF THE INVENTION

The invention relates to a method and a device for monitoring the concentration of a selected substance or group of substances in a body fluid of a living human or animal body.

A method for the above-mentioned purpose in which the substance or group of substances to be monitored is transferred from the body through an interface and away from behind the interface in a perfusion fluid flow, and in which the concentration of the substance or group of substances to be monitored in the perfusion fluid flow is measured downstream from the interface is known from International Patent Application publ. no. WO 89/02720.

The specific purpose of this known method is monitoring the glucose concentration in blood. The interface used is a subcutaneously inserted microdialysis membrane through which glucose diffuses from the blood into the perfusion fluid which is circulated at a flow rate of 100 to 1000 $\mu$l/hour and preferably between 200 and 400 $\mu$l/hour. Glucose which has entered the perfusion fluid is oxidized by oxygen in the perfusion fluid in the presence of a glucoseoxidase enzyme. The amount of $H_2O_2$ formed or the amount of $O_2$ consumed is determined, each of which are a measure of the glucose concentration in the perfusate and therefore an indication of the glucose concentration of the blood.

Information on the concentration of the selected substance or group of substances is obtained without having to take fluid samples each time information is desired. Moreover, the information can be provided continuously, so the concentration can be monitored with a minimal, constant delay.

The monitoring results can for example be used for watching over a patient and as input data for determining or correcting the dose of one or more substances to be administered to that patient, such as insulin and glucose (artificial pancreas).

The interface and the detector used in this known method are part of a wearable device, which furthermore comprises an enzyme metering system and a perfusion pump for driving the perfusate along the interface and the detector. Furthermore, the device will also need energy for the perfusion pump, which may for example be provided by a battery.

A problem of such devices is to provide a pump which provides a continuous constant flow, which is compact, not excessively expensive and of a simple reliable construction. Known pumps, although reasonably accurate over a longer period of time, typically generate a pulsatile or somewhat fluctuating flow. When a device with such a pump is used for monitoring, a pulsating or fluctuating measurement result is obtained. One tentative solution would be to cancel these variations out by calculating a running average over a sufficiently large window of time, but this would increase the measurement delay and reduce the time resolution and the sensitivity to peak values.

Furthermore, the weight and the dimensions of this known device have a negative impact on wearing comfort, cause the device to interfere with a patient's clothing and daily activities and increase the risk of damage to and dislocation of the device. A particular group of patients for whom size and weight of the device is very critical are neonates under intensive care in incubators. Such patients often weigh less than 2 kg. Another disadvantage of relatively substantial dimensions is that they limit the positions on the body where the device can be worn to some limited parts of the body which will not always be on or near preferred locations for the interface, such as on the forearm or the belly. If use is made of an invasively positioned interface, preferably widely varying locations should be available to avoid repeated damage to a limited area of a patient's body.

Because the device has a complicated structure, it is costly and relatively unreliable. Reliability is of particular importance if the monitored concentrations are used as input data for administering a substance such as a medicament.

In "An Enzyme-Selector for Electrochemical Monitoring of Choline and Acetylcholine: Applications in High Performance Fluid Chromatography, Brain Tissue, Microdialysis and Cerebrospinal Fluid" by Flentge et al. in Analytical Biochemistry 204, pages 305–310 (1992), an experiment is described in which enzymes are used for monitoring choline of a rat by brain dialysis. The device used in this small animal experiment also comprises a microdialysis interface which is placed intracerebrally. The flow rate of the perfusate is described to be 1 $\mu$l/min.

The device used in this experiment does not comprise means for metering enzymes, but the enzymes are physically immobilized between two membranes in a selector upstream from the detector. A pump for driving the perfusion fluid flow is also included in this device. This device is described as a laboratory set-up. A functionally identical dedicated device would be very large and would have a complicated structure.

In European patent application 0 134 758 a device is described in which a solution is pumped from a reservoir, through an implantable semi-permeable hollow-fibre circuit and to a sensor and then to a waste reservoir or back to the first-mentioned reservoir by means of a pump. To obtain an equilibrium between the concentrations of the substance to be monitored in the tissue and in the hollow-fibre circuit, the implantable hollow-fibre circuit has a great length. To enable implantation of the long hollow-fibre circuit, it is formed in a spiral shape sustained by a disk.

Since the hollow-fibre circuit has a substantial size, it has to be implanted surgically by making an incision in the skin and it has to be displaced at least every two weeks, which requires new surgery. Moreover, this device also comprises a pump and a battery which has to be relatively large to supply sufficient energy for pumping the solution through the hollow-fibre circuit. Both these items substantially contribute to the size and the weight of the device.

SUMMARY OF THE INVENTION

It is an object of the present invention to provide a method for monitoring the concentration of a substance or group of substances in a body fluid within a living human or animal, which does not require special surgery and can be carried out without large, complicated and expensive instruments.

According to the present invention, this object is achieved by providing a method of the above-identified type in which the flow rate of the perfusion fluid is less than 60 $\mu$l/hour.

Due to this relatively low flow rate, a very constant, i.e. non-pulsatile and substantially non-fluctuating flow can be maintained for a long period of time with simple means, which need no or very little supply of energy. The energy reservoir of the device can be very small and light because very little energy is needed for driving the perfusion fluid flow. The means for passing the perfusate from the interface to the detector can be of a simple, low-cost, reliable, compact and lightweight design and the volume of perfusate needed for monitoring during a given period of time is very small. Therefore the required structure of the device is substantially simplified, the device can be made substantially more compact and light and will be more reliable than the devices required for carrying out the known methods.

Calculation of a running average over longer time intervals to cancel out fluctuations of the measurement result caused by fluctuations of the flow rate is not required, so the measuring delay can be reduced, in particular if the cross-section of any conduit interconnecting the interface and the detector is reduced to maintain at least about the same flow velocity as in the known device but at the lowered flow rate according to the invention. A further contribution to reducing the measurement delay can be achieved, because the lowered flow rate according to the invention allows a more compact construction, so the distance between the interface and the detector can be reduced. In many cases the increased versatility regarding possible locations for the device on the body will allow a further reduction of the distance between the interface and the detector.

Obviously, the method according to the invention can also be used for monitoring other substances than glucose, choline and acetylcholine, e.g. lactate and ethanol if suitable selectors are used. Some substances may even be detected without using any selector. Experimental results indicate that while subcutaneous microdialysis can be used for on-line continuous monitoring of the concentration of extracellular substances, for the purpose of plasma lactate monitoring the interface should be placed intravascularly.

The invention can also be embodied in a device for monitoring the concentration of a substance or a group of substances in a body fluid of a living human or animal body comprising an interface, a detector, and means for maintaining a perfusion fluid flow from the interface to the detector. To carry out the method according to the invention, the means for maintaining a constant flow are designed for maintaining a flow of less than 60 $\mu$l/hour.

Particular embodiments of the invention are set out in the dependent claims.

Below some modes and embodiments of the invention will be described in more detail with reference to the accompanying drawings.

DETAILED DESCRIPTION OF MODES AND EMBODIMENTS OF THE INVENTION

Figure 1:
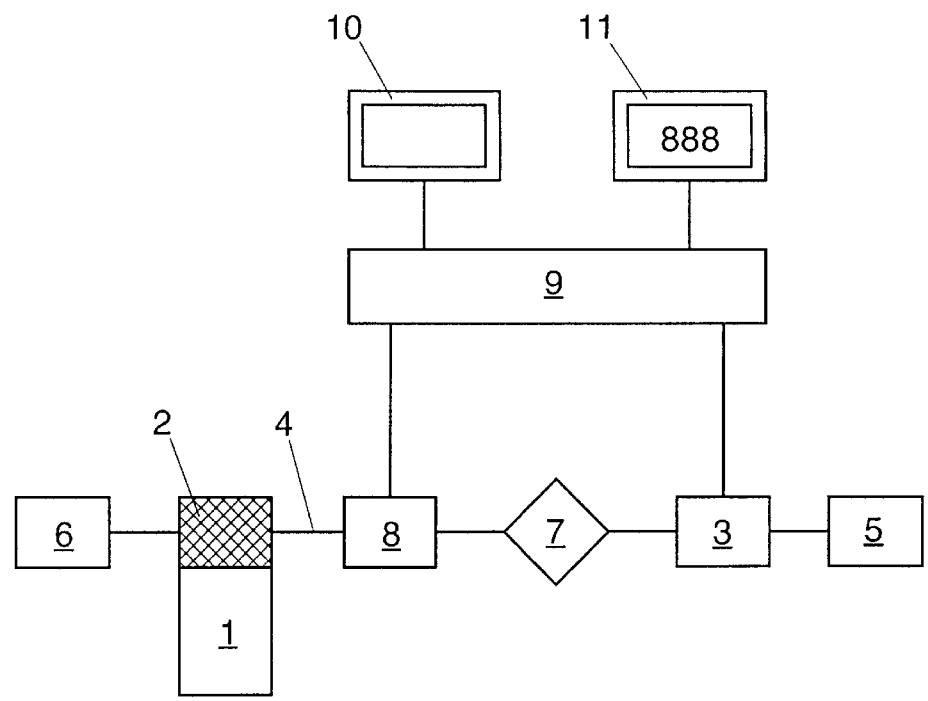
FIG. 1 is a functional diagram illustrating the invention.

The method diagrammatically depicted in FIG. 1 generally illustrates a preferred device for and mode of carrying out the method according to the present invention for monitoring the concentration of a substance or a group of substances in a body fluid of a living human or animal body. The preferred and other modes and embodiments will be described in a set-up and with settings adapted for monitoring the concentration of glucose. Examples of adaptations for detecting other substances are also described. Corresponding parts of different embodiments are designated by mutually identical reference numerals.

The human or animal body is designated by reference numeral 1. The device according to FIG. 1 comprises an interface 2, a detector 3, a flow channel or conduit 4 connecting the interface 2 to the detector 3 and means 5 for maintaining a flow along the interface 2 and the detector 3.

The device according to FIG. 1 further comprises a waste reservoir 5 and a supply reservoir 6 so that it can function completely independently of any stationary support devices. Instead of leading used perfusate to a waste reservoir, it may also simply be emitted out of the device.

Between the interface 2 and the detector 3 the device is provided with a selector 7 and a preoxidator 8 upstream from the selector 7. Control and processing electronics are generally depicted by rectangle 9 and communicate with the preoxidator 8, the detector 3, a recorder 10 and a display 11.

The interface 2 may for example be provided in the form of a microdialysis tube which is to be inserted subcutaneously. Such tubes are well known in the art. The tube can be made of saponified cellulose ester and may have an inner diameter of 0.22 mm and an outer diameter of 0.27 mm. Such tubes can be obtained from Cordis Dow Medical International, Brussels, Belgium.

The detector 3 is provided in the form of an amperometric electrochemical detector which may for example be equipped with a noble metal (e.g. silver, gold or, preferably, platinum) operating electrode and a silver/silver chloride reference electrode.

Structurally, the preoxidator 8 is essentially identical to an electrochemical detector but preferably has a relatively large oxidation surface and a potential which is set at a higher level than the potential of the electrochemical detector 3.

In the selector 7, a glucoseoxidase enzyme is physically immobilized between two cellulose nitrate membranes. The general principle of the glucose sensor is known and is based on the oxidation of glucose resulting in the formation of hydrogen peroxide in the presence of the glucoseoxidase enzyme.

The electronics 9 comprise potentiostats for maintaining a constant voltage over the electrodes of the detector 3 and the preoxidator 8. The recorder 10 is provided in the form of a memory of a microprocessor, so that the contents of the memory can be read into an external device for review and analysis.

In operation, a perfusate is passed from the supply reservoir 6 to the interface 2 where inter alia glucose penetrates the interface 2 into the perfusate. The amount of glucose penetrating the interface 2 depends on the concentration of glucose in the blood within the body 1. The glucose which has penetrated the interface 2 is entrained by the perfusion fluid along the preoxidator 8 where oxidizable substances—which would disturb the measuring result obtained at the detector 3—are deactivated before hydrogen peroxide is formed. If the glucose concentration is to be monitored, the potential over the preoxidator is preferably set at a voltage of about +750 mv.

When the glucose subsequently reaches the selector 7, it is oxidized in the presence of the enzyme in the selector and a quantity of hydrogen peroxide proportionate to the amount of glucose which has entered the selector 7 is formed.

The perfusate with the hydrogen peroxide is then led to the electrochemical detector 3 in which a potential difference (for this application preferably about +250 mV) is maintained so that the hydrogen peroxide is oxidized causing a current over the electrodes which is proportionate to the amount of hydrogen peroxide that is oxidized in the detector 3. The current is measured by the processing part of the electronics 9. From that current a signal representing the glucose concentration in the blood is calculated in accordance with a function stored in the electronic processor 9. The signal is stored by the recorder 10 and displayed by the display 11.

The flow rate is maintained at a level of less than 60 $\mu$l/hour and preferably at a level of less than 25 $\mu$l/hour. The most preferred flow rate is less than 20 $\mu$l/hour (0.33 mm$^3$/min) and presently held to be about 5–9 $\mu$l/hour, but for some applications the perfusate may be passed from the interface to the detector at a flow rate as low as 1 $\mu$l/hour.

Due to these low flow rates, a very constant flow can be maintained for a long period of time with simple means, which need no or very little supply of energy. In the preferred embodiment, the means for maintaining the flow of the perfusate are of a non-moving type and consist of a waste reservoir 5 containing a fluid absorbing material and communicating with the detector 3 and the interface 2 via the conduit 4. The fluid absorbing material may for example be a silica gel with a particle size of 40–120 $\mu$m. Also dehydrated crystals such as copper sulphate or sponge-like materials may be used for drawing the perfusion fluid through the conduit 4.

A separate energy reservoir for the purpose of driving the flow can thus be dispensed with or be very small and light. The reservoir containing dehydrated crystals forms a simple, low cost, reliable, compact and lightweight design.

According to another embodiment of the invention, the means for maintaining the constant flow along the interface 2 and the detector 3 comprise a gas filled excess pressure or vacuum reservoir in the supply reservoir or in the waste facility, respectively. Since only very little fluid has to be passed—at 10 $\mu$l/hour, 1 cm$^3$ of perfusate is sufficient for more than four days—a relatively small excess pressure or vacuum reservoir will be sufficient for maintaining a sufficiently constant flow.

The vacuum reservoir may for example be a replaceable cartridge containing a vacuum and which becomes operative when it is coupled to the monitoring device. Such cartidges are commercially available at low cost and widely used for obtaining blood samples from patients.

If the means for maintaining a constant flow comprise driving means located downstream of the detector and adapted for drawing perfusate from the interface to the detector, for example in the form of the above-described vacuum cartridge and a restriction for controlling the flow rate, this restriction is preferably located between the detector and the driving means. One advantage of this arrangement is that the pressure drop to which the substances extracted from the body are subjected before having passed the detector is limited. Such a pressure drop enhances the formation of bubbles of gas which was dissolved in the perfusion fluid. Gas bubbles would cause undesirable fluctuations of the measuring result. Nevertheless a slight pressure drop is advantageous for supporting the passage of substances through the interface.

If necessary, the pressure difference between the supply and the waste reservoir can be supported by resilient means and/or regained by pumping or reloading from an external source. The pressure difference may be detected and a signal corresponding with the detected pressure difference may be generated to take into account the effect of a decreasing pressure difference on the flow rate when processing the signal from the detector 3. Alternatively, if a perfusate containing relatively large amounts of oxidizable substances is used, the flux of oxidizable substance passing the preoxidator 8 provides a measure of the flow rate of the perfusate. The electrical current passing the preoxidator 8 is proportionate to that flux and therefore also to the flow rate. Thus the electrical current passing the preoxidator 8 can be used for monitoring the flow rate and as an input representing that flow rate for calculating an estimate of the concentration in the perfusion fluid, and consequently in the body fluid, from the signal obtained from the detector 3.

Apart from the above-described embodiments, there are many other possibilities for providing non-moving means for maintaining a constant flow, such as a capillary reservoir forming the waste facility, an osmotic membrane and a heater for warming up an expansion element adjacent the supply reservoir.

The above described effect that the volume of perfusate required for monitoring during a given interval of time is very small (at most about 1 cm$^3$ per 24 hours) is of course also advantageous in itself.

In summary, the required structure of the device is substantially simplified, can be made substantially more compact and light and will be more reliable than the devices required for carrying out the known methods, in which substantially larger flow rates were used.

The conduit 4 interconnecting the interface 2 and the detector 4 preferably has a relatively small diameter to increase the flow speed at a given flow rate, so that the delay between passage of a substance through the interface 2 and detection at the detector is minimized and longitudinal diffusion of substances dissolved in the perfusate, leading to a similar effect as calculating a running average, is limited. The conduits interconnecting the pick-up element and the detector preferably have a diameter of less than 0.2 mm so that the effective cross-sectional surface is less than about 0.02 to 0.03 mm$^2$, depending on the shape of the cross-section. Conduits with a cross-section of about 0.0045 mm$^2$ (e.g. with a circular cross-section having a diameter of about 0.075 mm) are most preferred and provide a quick throughput of perfusion fluid (e.g. a speed along the conduit of 44 mm/min at 12 $\mu$l/hour) without causing excessive resistance at the envisaged flow rates and are preferably provided in the form of fused silica tubing.

Thus a reduced measuring delay can be achieved in spite of the reduced flow rate, because the lower flow rate allows a more compact construction of the device while the flow speed can be maintained at substantially the same level. In many cases a further reduction of the distance between the interface and the detector can be achieved since a smaller device can be mounted to and worn at places on the body where larger devices cannot be worn.

If an interface 2 in the form of a subcutaneously inserted dialysis probe is used, the slow progression of the perfusion fluid along the interface caused by the low flow rate according to the invention brings about the advantage that at downstream portions of the dialysis membrane interface an equilibrium between the concentrations of at least the substance or group of substances to be monitored in the body fluid and in the perfusion fluid will be reached or approached. At that equilibrium the flux of substance penetrating the interface 2 into the perfusion fluid is equal to the flux through the interface 2 in the opposite direction. Therefore, disturbing influences caused by the resistance of the interface membrane and the withdrawal of substances from the body fluid to be monitored—which causes concentration gradients in both the body fluid and the perfusion fluid—will be minimized, so a more accurate measuring result is obtained. In particular, such gradients are difficult to predict during in-vivo monitoring and cannot be corrected by calibration based on in-vitro experiments, since tissue characteristics rather than microdialysis variables determine the in-vivo recovery of the concentration of a substance in a tissue. When the concentration of a substance in blood is monitored, calibration requires analysis of blood samples containing different concentrations of the substance or substances to be monitored.

Another possibility which arises due to the low flow rate is to refrain from feeding any perfusate to the interface from a reservoir, but to obtain perfusate consisting of constituents of the body fluid by letting body fluid pass through the interface. The passage of body fluid through the interface may involve a dialysis process. However, in some applications it is also conceivable to simply let the body fluid pass through an interface in the form of an open window without any selection at the interface, for example if the body fluid in which a concentration is to be monitored is a secretion from the body which does not contain any substances which would disturb the selection and detection process.

If for selection of the substances to be monitored an immobilized reaction material such as enzymes is used, a further advantage of a low flow rate is that the amounts of the substances or groups of substances to be monitored that are entrained by the perfusion fluid are smaller than in the known methods and devices, in which the perfusion flow rates are higher. For example, in a set-up in which the perfusate is mainly passed along the interface in the form of a dialysis membrane, the more the equilibrium of concentrations in the fluids at opposite sides of the membrane is approached, the more the substance or substances to be monitored migrate back into the body fluid instead of being carried along by the perfusate or being oxidized in the presence of an enzyme dissolved in the perfusate. Due to the low net flux of substances to be monitored through the interface 2 during a given period of time, the amount of reaction material required per period of time is correspondingly low. This allows, for example, dispensing with enzyme metering means and using a small selector 7.

If input of a reaction in the selector 7 comprises a reactant dissolved in the perfusate (e.g. oxygen) other than the substance to be monitored, the supplied amount of that reactant in the perfusate must be sufficient for reaction of the selected substance to be monitored (e.g. glucose) received in the perfusate, so that the reaction is not limited by the flux of that reactant available for the reaction. It is known to provide a high flow rate of the perfusate for this purpose, so that a relatively low concentration in the perfusate of the substance to be monitored is obtained.

According to a particular mode of carrying out the present invention, the problem of providing sufficient reactant (e.g. oxygen) is solved by carrying out the reaction in such a manner, that only a known fraction of the flux of the selected substance to be monitored is consumed in the selector and the remaining fraction thereof passes the selector without reacting. The known reacting fraction of the substance is maintained at such a level, that a remainder of the other reactant passes the enzymes without reacting also, i.e. such that the other reactant is not totally consumed. Thus the flux of the detectable reaction product (e.g. $H_2O_2$) generated from the reacting fraction of the arriving substance to be monitored varies with the concentration of that substance in the perfusate and can thus be used as a measure of the concentration of the substance to be monitored in the perfusate upstream from the selector.

The fraction of the flux of the substance to be monitored reacting in the selector can, for example, be controlled by providing a limited amount of enzymes or by passing a fraction of the perfusate by the space in which the enzymes are immobilized while allowing diffusion of particularly the reactant other than the substance to be monitored from the perfusate passing by the space in which the enzymes are immobilized into that space, as will be described hereinafter in more detail.

Instead of a subcutaneous interface, a transcutaneous non-invasive interface which is held against the skin can be used. An essential advantage of the use of such an interface is that it is not necessary to penetrate into the patient. In such devices the interface is preferably provided in the form of a membrane to keep undesired substances out of the perfusion fluid. However, such an interface may also be provided in the form of an open window which is to be held against the skin.

A problem of transcutaneous interfaces is generally that the flux of the substance or substances to be detected is relatively small, resulting in low concentrations of the substances to be monitored in the perfusate and therefore a relatively low sensitivity. Due to the low flow rate according to present invention, the ratio between the concentration of a substance to be monitored in the perfusate and the concentration of that substance in the body fluid—typically referred to as the microdialysis extraction fraction—is substantially higher than at the usual higher perfusate flow rates, so the sensitivity of the measuring method is accordingly increased.

Examples of transcutaneous interfaces 2 are described in International Patent Application PCT/NL 93/00086 and also in a publication entitled "Continuous Monitoring of Glucose with a Transcutaneous Microdialysis Probe" by De Boer, Plijter-Goendijk and Korf in Lancet 340 (1992), pages 547–548.

As in the known methods where the perfusion is passed at higher flow rates, the method according to the invention, too, can be used for monitoring other substances than glucose, provided suitable selectors are available. Selectors for detection of lactate, ethanol and choline are, for example, described in "On-line Real Time Monitoring of Extracellular Lactate, Ethanol, Glucose and Choline using Microdialysis and Enzyme Selectors" by Korf et al. in: "Techniques in the Behavioural and Neural Sciences", Robinson and Justice (eds.), Elsevier Science Publ. Cie., Amsterdam, New York (1991), pages 349–368.

Other conceivable applications are controlled administration of cytostatics, intravenously administered anaesthetics, administration of theophylline to newborn babies with breathing problems and monitoring of the concentrations of the cortisol, the adrenaline and the peptide adrenocortitrope hormone in patients suffering from depressions.

Preferably, the enzymes are immobilized in the selector 7 between membranes. Such selectors are compact, fast and very sensitive. Material to which the enzymes are bound is not required, so a large quantity of enzymes can be immobilized in a very small space. Other advantages of this type of selector are that the enzymes are very stable when kept under appropriate conditions, low cost, avoidance of enzyme inactivation by chemical immobilization, and easy preparation and maintenance.

A very versatile and specific selecting means is obtained if, instead of the enzymes, a complex of an antibody and an antibody-specific derivative of the substance to be monitored, which is detectable by a detector, is immobilized in the space between the membranes. Another advantage of such a selector is that it does not rely on any reactant dissolved in the perfusate (such as oxygen) for selecting the substance to be monitored, so high concentrations of the substance to be monitored can be allowed without having to take special measures to avoid limitation of the measured concentration of the substance to be monitored due to a lack of a reactant.

A derivative as described above should have less affinity to the antibody than the substance to be monitored and may be tagged to facilitate detection. Generally, the tagging will inherently bring about the required reduction of the affinity to the antibody. When the substance to be monitored reaches the complex, it substitutes the derivative which is entrained by the perfusate through the membrane bounding the space and detected downstream by the detector. The amount of detected derivative is proportionate to the amount of substance arriving in the selector space. The detector is preferably an electrochemical detector as described earlier, because such a detector is compact and of simple construction. However, in principle also other combinations of tagging and suitable detectors can be used to make use of other detection principles, such as fluorometry, chemiluminescence and radiometry. Such detection principles may also be applied if the selector contains enzymes.

The substitution, tagging and detection principles are as such well known, for example from immunoassay measurement techniques and a wide variety of kits for carrying out these techniques is commercially available. However, as far as the applicants are aware, such immuno-reaction methods have thus far only been applied off-line and were therefore not suitable for monitoring.

When after some time too much of the antibody has been occupied by the substance to be monitored, the selector can easily be reloaded by passing an excess amount of the derivative through the selector. Alternatively, the contents of the selector may simply be replaced by a fresh complex of antibodies and derivatives. If a selector containing a complex of antibodies and derivatives of the substance to be monitored as described above is used, it is particularly advantageous that in the method according to the invention relatively small amounts of reaction material are consumed per unit of time, because many of these complexes are extremely expensive and on the other hand reloading the selector is a quite cumbersome procedure.

Substances which can be selected using a complex of antibodies and derivatives of the substance to be monitored are typically substances of which the concentrations in the patient are very low, such as hormones and medicaments. Particularly for such applications the above-described effect that the ratio between the concentration of a substance to be monitored in the perfusate and the concentration of that substance in the body fluid is substantially higher than at the usual higher perfusate flow rates, is very advantageous because it brings about an increased measuring sensitivity.

Antibodies may include polyclonal as well as monoclonal antibodies and also antigen binding fragments thereof, which may have been obtained by purification from material generated by an animal or recombinant methods. Fab and Fab'2 fragments can be obtained simply by chemical splitting. Smaller binding fragments down to molecular recognition units (which only consist of a complementary determining region) are usually prepared by DNA recombinant methods. DNA recombinant methods can also be used to prepare antibodies with two specificities or coupled to other proteins. Also enzymes can in principle be provided in the form of whole enzymes or fragments thereof and may be obtained by purification or recombinant methods.

In FIGS. 2–5 some devices for carrying out the method according to the invention are shown in more detail.

Figure 2:
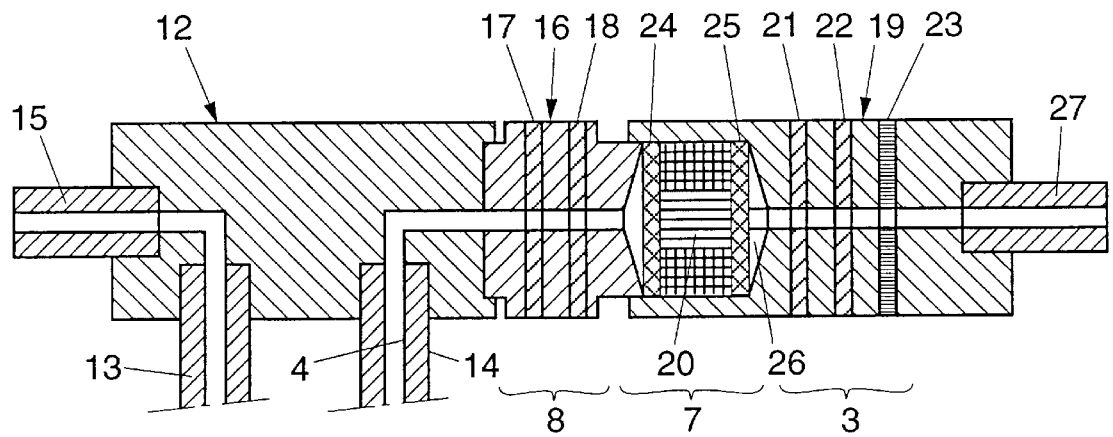
FIG. 2 is a schematic view in cross-section of a pick-up and detection module for use in a device according to the invention.
Figure 3:
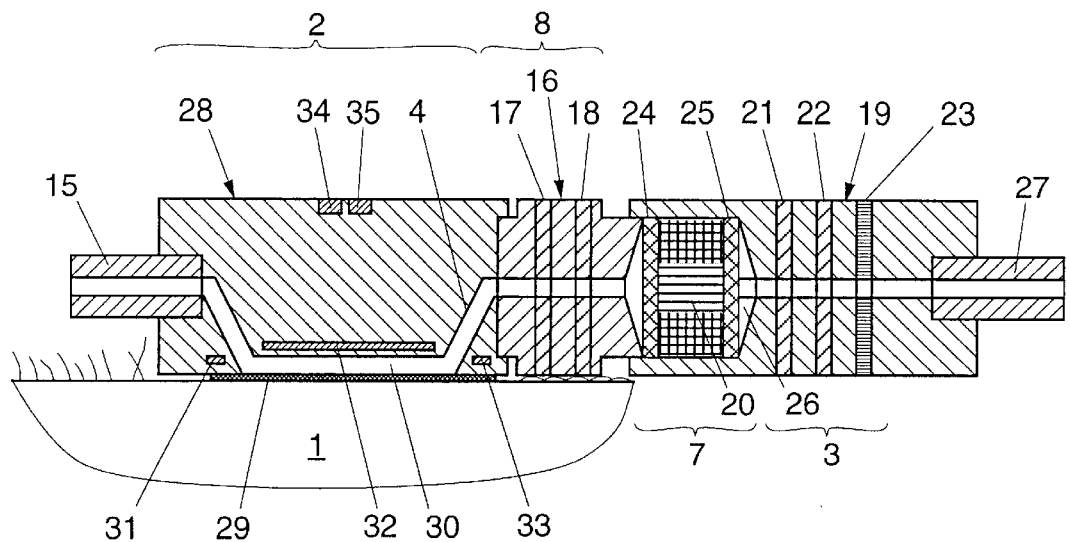
FIG. 3 is a schematic view in cross-section of another pick-up and detection module for use in a device according to the invention.

In FIGS. 2 and 3, pick-up and detection modules for use in a device according to the invention are shown which are each composed of three modular bodies of plastic material (e.g. polyoxymethylene).

In the device shown in FIG. 2, the upstream (left hand) body 12 forms a coupling to which an interface can be coupled by means of a tubing 13, 14. A conduit to the supply reservoir can be connected to the nipple 15.

The central body 16 is of a sandwich construction and contains two electrodes 17, 18 of the preoxidator 8. The electrodes can for example be made of glassy carbon and carbon/polytetrafluorethene (35%/65%). Such a body can efficiently be manufactured by interleaving the layers of material of the plastic material and the material of the electrodes and drilling the conduit 4 through the multilayered material. The bore for forming the respective conduit section preferably has a diameter of 0.075 mm. A larger diameter, e.g. 0.3 mm, may be preferable if the electrodes extend in the conduit, so that the conduit is narrowed at the electrodes. To keep the layers of the preoxidator in alignment, an adhesive may be applied before the layers are placed onto each other. Alternatively, for example bores with two or more alignment rods or a shell around the composition of layers can be provided. If a preoxidator 8 is not required, a single piece of plastic of a corresponding shape can be provided instead of the shown body 16.

The downstream body 19 contains a chamber 20 of the selector 7 and three electrodes 21, 22, 23 of the detector 3. The chamber 20 contains or is to contain the selecting material such as the enzymes or the complex of antibodies and derivatives of the substance or group of substances of which the concentration is to be monitored. The body 19 has a layered structure similar to that of the body 16 and can be constructed in essentially the same manner. The chamber 20 is bounded by two membranes 24, 25 and walls of the downstream body 19. The reaction material in the space 20 is sandwiched between the membranes 24 and 25. If the reaction material is provided in the form of a relatively thick zone as shown in FIGS. 2 and 3, it may be useful that the chamber also contains a permeable filler to reduce the resistance encountered by the perfusate upon passing the chamber 20. The upstream membrane 24 is held against the reaction material by the downstream face of the central body 16, which has a negative conical shape to allow distribution of fluid arriving through the conduit 4 over the upstream membrane 24. The downstream membrane 25 is supported by flanges 26 at its downstream side to avoid wrinkling of the membrane under influence of the pressure of the flow of the perfusate.

The upstream and the central electrodes 21, 22 of the detector 3 are of platinum and are the operating electrodes. The downstream electrode 23 is a silver/silver chloride reference electrode.

At the downstream end of the downstream body 19 a nipple 27 is provided to which a conduit to the waste reservoir can be connected. The waste reservoir may contain an oxidizing substance such as ascorbic acid to catch away $H_2O_2$ gas which may have been formed in the selector and would otherwise occupy too much space.

The device shown in FIG. 3 differs from that in FIG. 2 in that instead of the upstream body 12 an upstream body 28 is provided. The upstream body 28 comprises a transcutaneous interface with a membrane 29. The portion 30 of the conduit 4 behind the membrane 29 has an enlarged width to obtain an interface having a sufficiently large window of interaction with the skin.

The upstream body further comprises resistor elements 31, 32, 33 for thermostatically heating the area of the window of interaction to a temperature slightly above the range of normal skin temperatures of the patient, so that it is ascertained that the temperature of the skin in the area of the window of interaction is kept constant during the monitoring period. Contacts 34 and 35 are provided for delivering current for the resistors 31, 32, and 33.

Figure 4:
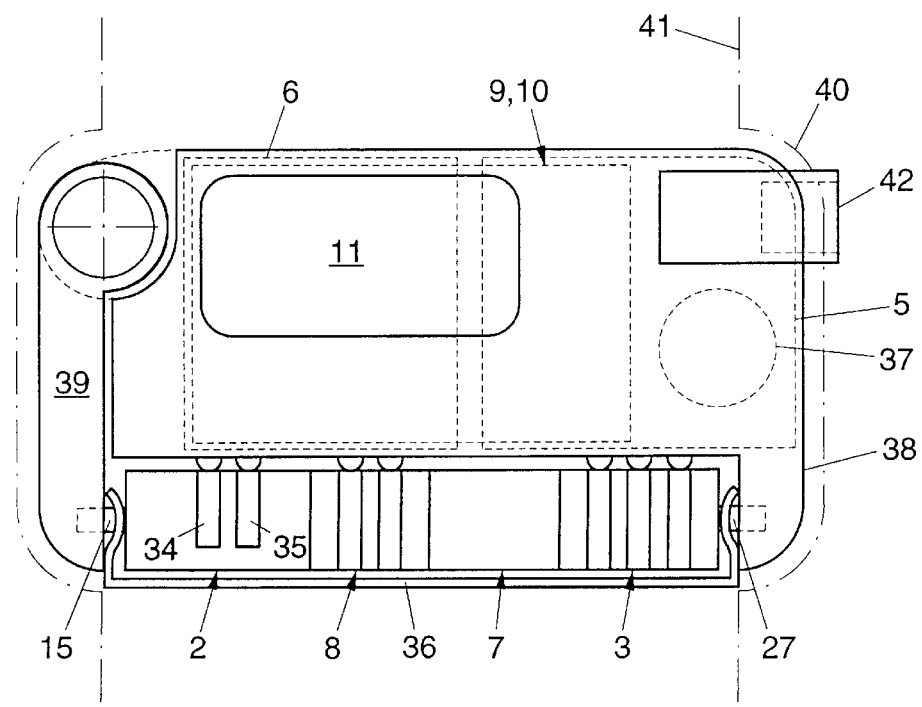
FIG. 4 is a top plan view of a device according to the present invention in which a pick-up and detection module according to FIG. 3 is incorporated.

In FIG. 4 a device according to an embodiment of the invention is shown, in which the pick-up and detection element shown in FIG. 3 is incorporated. The modular bodies are axially pressed against each other by a resilient element 36. The supply reservoir 6, the waste reservoir 5, the electronics 9 including a recording memory 10, a display 11 and a battery 37 are positioned in a housing 38 of compact dimensions. The housing 38 is further provided with an orifice (not shown) into which the downstream nipple 27 is removably inserted. The upstream nipple is removably inserted in an orifice (not shown) which is provided in the free end of a pivotable arm 39. For mounting the pick-up and detection module, first the pivotable arm 39 is pivoted away from the housing 38. Then the pick-up and detection module is positioned so that the downstream nipple 27 is in front of and axially aligned relative to the orifice in the housing 38 and the nipple is inserted into the orifice by axially moving the pick-up and detection module towards the orifice. Subsequently, the connection of the upstream nipple 15 to the orifice in the pivotable arm 39 is made by pivoting the arm 39 towards the pick-up and detection module until it abuts against the upstream nipple 15.

The device further comprises a port 42 for connecting an input and/or output device such as an external device for programming the device with calibration data or a device for administering insulin and glucose on the basis of glucose concentration data received from the device.

The device shown in FIG. 4 further comprises means for mounting the device to the body in the form of a cover 40, which is shown in dot and dash lines only, and which is provided with flaps 41 which can be attached to the skin by a plaster, so that the device can be worn on any desired part of the body. Alternatively, the cover can for example be provided with a strap to mount the device to an arm or a leg in a manner similar to the way a wrist-watch is worn. Preferably, the cover is provided with a window in front of the display 11 and an opening through which a plug can be inserted.

In many applications it is important that the perfusion fluid and the selector 7 are maintained at a constant temperature. Since the shown device is adapted to be mounted to the body (preferably but not necessarily directly on the body), in use the selector included in it will also be worn on the body. This brings about that the temperature of the selector is to a large extent regulated by the temperature of the body, so means for keeping the temperature of the selector constant are not required or need only have a very limited capacity. Energy consumption of the device is accordingly reduced.

The temperature of the selector 7 and the perfusate can particularly effectively and efficiently be maintained at a constant level if the selector 8 is thermally insulated from the environment of the body. To obtain this insulation, in the shown device, the cover 40 is provided with insulating material so that it forms a thermally insulating layer which covers the device and leaving free a side of the device which is to be worn in a position facing the body, when it is in mounted position. A constant temperature of the perfusate and of the reservoirs and the conduit containing the perfusate is advantageous for obtaining a constant flow rate of the perfusate which is not disturbed by thermal expansion and shrinkage of the perfusate, the conduit and the reservoirs. This is particularly important if the conduit is extremely elongated, i.e. of a small cross-section in comparison with its length.

When the cover 40 is in mounted position, it forms a thermally insulating layer which also covers the transcutaneous interface 2. Due to this insulation, very little energy is required to maintain the temperature of the skin in the area of the interface on the level which is slightly elevated relative to the range of normal skin temperatures.

To further reduce the dimensions and the weight of the device, it can be provided with a common thermostatic heater for keeping both the selector and the skin in the area of the pick-up element at a constant temperature slightly above the range of normal body temperatures.

Figure 5:
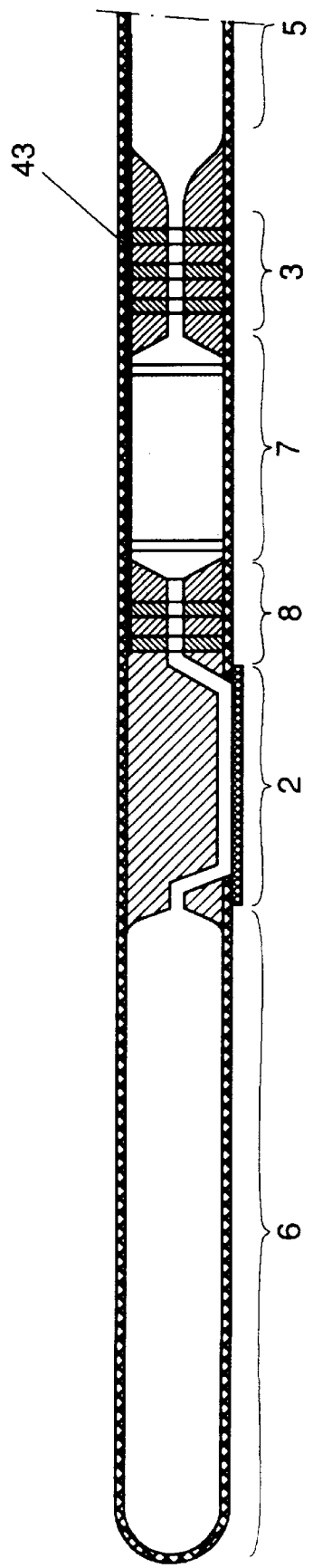
FIG. 5 is a schematic view in cross section of a catheter in which a pick-up and detection module for use in a device according to the invention is incorporated.

FIG. 5 shows a pick-up and detection module of a device according to the invention, which is incorporated in a catheter. Since a catheter is generally not maintained in the body of the patient for a very long time and the flow rate of the method according to the invention is very low, the detector 3 as well as the supply and the waste reservoirs 6 and 5, respectively, can be very compact so that these parts can be located in the catheter and supply and return conduits extending along the catheter are not needed. Moreover, a very quick response of the detector 3 is achieved since the detector 3 can be positioned very close to the interface 2. The embodiment shown in FIG. 5 is also provided with a preoxidator 8 and a selector 7. Also these parts of the device can be made sufficiently compact to be positioned within the catheter due to the low flow rate of the method according to the invention and the correspondingly low capacity requirements these parts have to fulfil. Electrical connections generally designated by reference numeral 43 extend from the preoxidator 8 and the detector 3 in a direction away from the free end of the catheter. To obtain an increased reliability of the device and less susceptibility to interference, a part of the electronics may also be located within the catheter immediately adjacent the detector 3.

Figure 11:
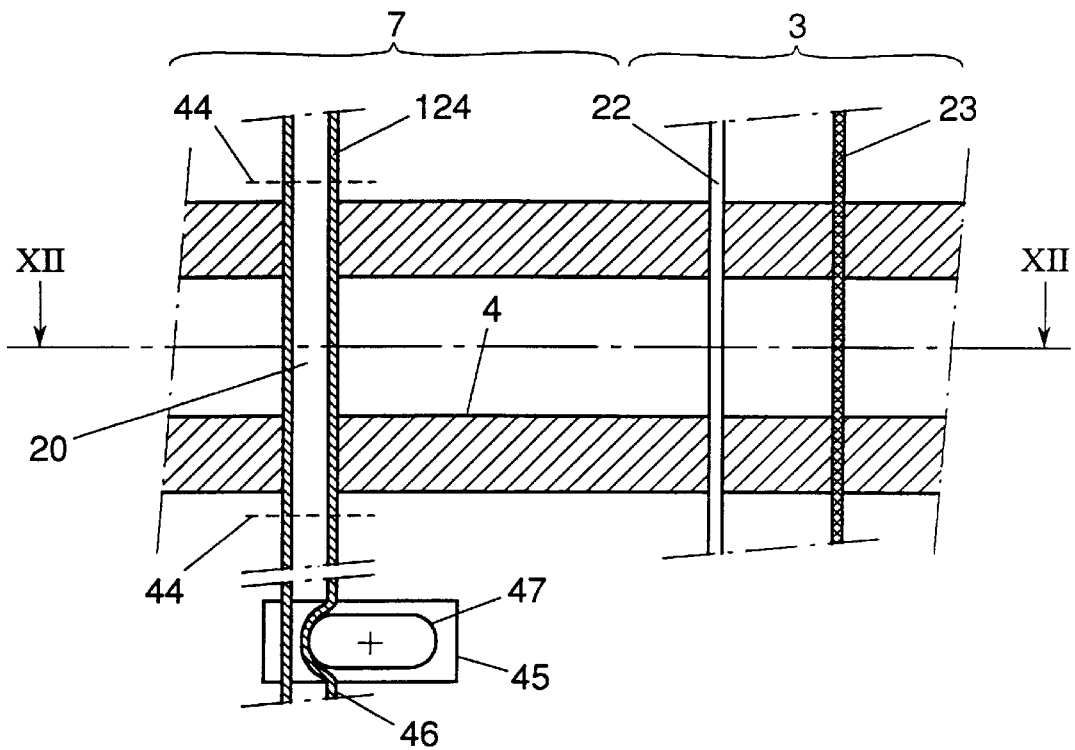
FIG. 11 is an enlarged schematic side view of yet another detection module for use in a device according to the invention.
Figure 12:
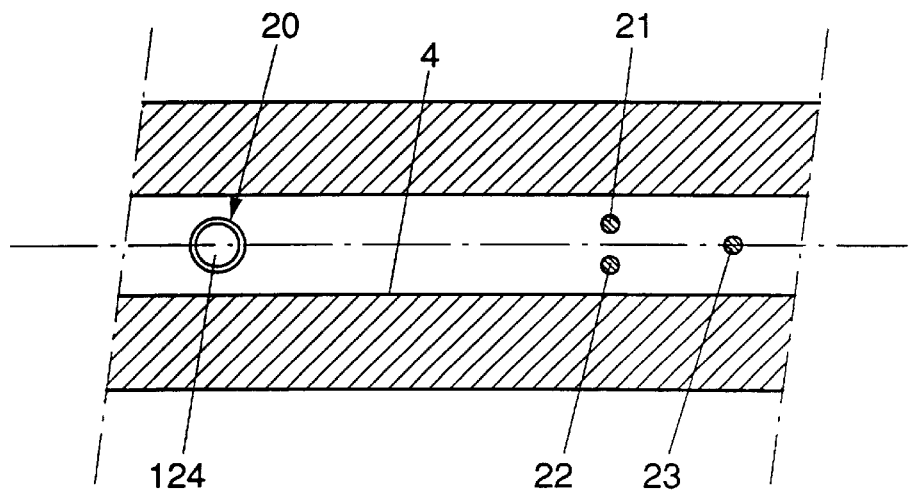
FIG. 12 is a view in cross-section along the line XII—XII in FIG. 11.

The main structure of a currently most preferred embodiment of the device according to the present invention is shown in FIGS. 6–10. FIGS. 11 and 12 show alternative more preferred structures for the selector and detector which may be incorporated in the device shown in FIGS. 8–10 instead of the structures shown in FIGS. 6 and 7.

In this device the conduit 4 downstream from the interface is bounded by a tygon tubing having an inner diameter of about 0.3 mm. A selector 7 is provided in which reaction material is immobilized in a dialysis fibre 124 (inner diameter about 0.1 mm, outer diameter about 0.2 mm) of which the ends are sealed and which extends through the conduit 4. The dialysis fibre 124 extends axially within the conduit, so a relatively large effective chamber 20 is obtained.

Since the dialysis fibre 124 fits in the conduit 4 with some clearance, in use perfusion fluid partially passes by the chamber and partially passes through the chamber 20. Where the device is used for the detection of glucose, only an essentially constant relative fraction of the total glucose flux enters into the chamber—either with perfusion fluid penetrating the wall of the dialysis fibre or by diffusion through the dialysis fibre—and reacts under influence of the enzyme immobilized in the dialysis fibre. Oxygen diffuses more rapidly than glucose, so the relative fraction of the total oxygen flux through the conduit 4 entering the chamber 20 is larger than the above-mentioned relative fraction of the total glucose flux through the conduit 4 entering the chamber 20. Due to this effect, at higher glucose concentrations in the perfusion fluid, which particularly occur at low flow rates according to the present invention, limitation of the amount of hydrogen peroxide formed due to lack oxygen available for the reaction is avoided. It is noted that it is essential for the above-described effect, that the flow speed of the fluid passing the selector 7 is on the one hand sufficiently low to allow substantial amounts of oxygen to diffuse into the chamber, but on the other hand sufficiently high to prevent diffusion of too large amounts of glucose into the chamber 20. of course the above-described effect can also be used with other substances to be monitored and other reactants, provided the reactant other than the substances to be monitored diffuses more rapidly through the perfusion fluid than the substance or group of substances to be monitored.

If the molecule size of the substance to be monitored is substantially larger than that of the other reactant, selective diffusion from the perfusate passing by the chamber in which the enzymes are immobilized into that chamber can also be obtained by providing a part of the chamber with porous walls having such a pore size that the other reactant can penetrate the walls at least more easily than the substance to be monitored.

Another advantage of the arrangement in which a clearance is present between the chamber 20 and the walls of the conduit 4 is that a large amount of reaction material can be provided, without causing a high flow resistance. The perfusate can pass by the chamber 20 and interact with the chamber by diffusion through the porous walls of the chamber 20 essentially without actually flowing through the chamber 20.

The detector 3 comprises electrodes 21, 22, 23 of the same material as described above, but provided in the form of wire-shaped pins which are pinched through the walls of the conduit 4 and extend transversely through the conduit. The wires 21, 22, 23 each have a diameter which is substantially less than the diameter of the conduit 4 (e.g. less than 80%). Preferably the diameter of the electrode pins is about 0.12 mm. The spacing between the wires 21, 22, 23 is preferably between 0.05 and 2.5 mm in longitudinal direction of the conduit 4.

At low flow rates it is very important that the surfaces of the conduit and the electrodes are very smooth in order to reduce the tendency of bubbles of gas to cling to the material bounding the conduit and to the electrodes. Such bubbles disturb the measuring result. In the selector 7 and the detector 3 shown in FIGS. 6 and 7, a very smooth surface of the electrodes and the walls of the conduit 4 can easily be obtained. The tygon tubing is manufactured by extrusion or drawing so that it is relatively easy to obtain a smooth inner surface. The electrodes 21, 22, 23 can easily be polished, because the polishing process can be carried out on the outside thereof.

Since the conduit 4 is narrowed adjacent the electrodes, all the perfusion fluid passes closely by the electrodes 21, 22, 23 providing an opportunity to interact with the electrodes for a large portion of the constituents of the perfusion fluid. This effect is particularly useful in the present invention because due to low flow speeds, the flow along the electrodes is of a laminar nature, so the fluid is mixed very little.

Another advantage of the narrowed passage at the electrodes 21, 22, 23 is that the flow speeds along the surfaces of the electrodes are relatively high, so bubbles clinging to the electrodes 21, 22, 23 are flushed away more effectively.

The selector 7 and the detector 3 can be manufactured in a very simple manner from commercially available parts. This reduces the manufacturing costs of the device to an extent which makes its use as a disposable or partially recyclable instrument attractive.

Figure 6:
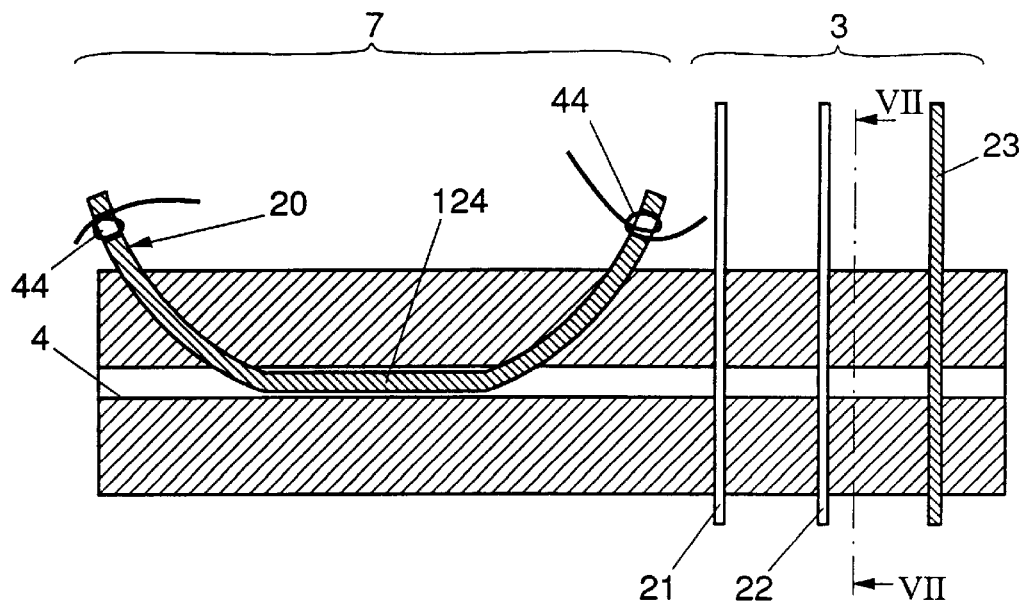
FIG. 6 is an enlarged schematic side view of yet another detection module for use in a device according to the invention.
Figure 7:
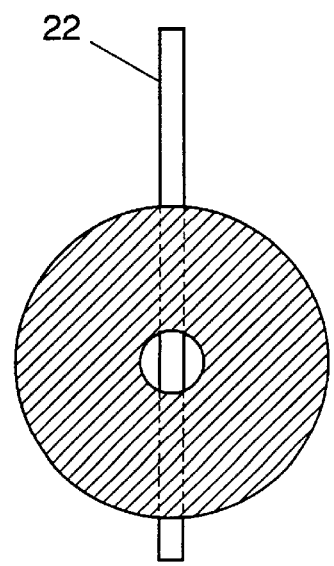
FIG. 7 is a side view in cross-section along the line VII—VII in FIG. 6.

During experiments with the device shown in FIGS. 6 and 7, at a flow rate of 6 $\mu$l/hour and a glucose concentration in the perfusion fluid of 5 mmol, a current of 7 nA over the electrodes was measured at a potential of 500 mV. When the flow rate was lowered, the current increased.

Another advantageous effect which occurs at very low flow rates when electrodes 21, 22, 23 are positioned closely behind the chamber 20 is that $O_2$ which is formed at the electrodes is allowed to diffuse upstream into the chamber 20 and to react again in the presence of the enzymes to form hydrogen peroxide. This also contributes to solving the problem of lack of oxygen in the perfusate.

The simple design and ease of manufacture of the detectors and the selectors generally as described above with reference to the FIGS. 6 and 7 is advantageous for many other applications, such as in-vitro measurements and in general where miniature low cost detectors and/or selectors are needed. Particularly the possibility of simply immobilizing enzymes or a complex of antibodies and derivatives of a substance of which a concentration or the mere presence is to be determined is advantageous for many applications.

The presently most preferred structure shown in FIGS. 11 and 12 differs from the structure shown in FIGS. 6 and 7 in that the dialysis fibre 124 extends transversely from one side to the oppsoite side of the conduit 4 and in that the platinum operating electrodes are arranged laterally spaced from each other in a direction perpendicular to the conduit 4.

Since the dialysis fibre 124 is arranged transversely through the conduit 4, assembly of the structure is facilitated and the operative wall surface of the dialysis fibre 124 is easily controlled. The amount of selective medium in the part of the dialysis fibre 124 within the conduit is smaller than in the structure shown in FIGS. 6 and 7. However, this disadvantage can easily be overcome by axially displacing the selective medium within the dialysis fibre 124 or by axially displacing the dialysis fibre 124 in which the selective medium is immobilized. For axially displacing selective medium within the dialysis fibre 124, a peristaltic pump 45 cooperating with a conduit 46 is provided. The cross-section of the conduit 46 and a rotatable member 47 of the peristaltic pump are dimensioned such that a predetermined number of rotations of the rotating member 47 provide the required axial displacement for replacing selective medium in the chamber 20. The peristaltic pump 45 can for example be driven manually every 24 hours using a special key. In operation, the dialysis fibre 124 is preferably closed off closely adjacent the walls of the conduit 4 to prevent draining along the dialysis fibre 124. In some applications it may also be sufficient to close off the dialysis fibre further away from the walls of the conduit 4.

Due to the position of the operating electrodes 21, 22 laterally spaced in the same cross-section of the perfusate flow, the conduit 4 is particularly effectively narrowed adjacent the operating electrodes, so the perfusion fluid passing between the operating electrodes 21, 22 interacts particularly effectively with the electrodes and bubbles clinging to the electrodes 21, 22 are flushed away particularly well. Since the section of the fluid flow which determines the electrical current over the operating electrodes 21, 22 is relatively short in flow direction, a very rapid and direct response to fluctuations of concentrations of the substance to be monitored in the fluid flow is obtained. Moreover, disturbances caused by diffusion, occurring as fluid flows from one operating electrode to the other, is eliminated.

If it is desired to leave a somewhat larger cross-section free for the fluid to pass, the electrodes may also be spaced from each other in a direction oblique to the axis of the conduit 4. However, as the direction in which the electrodes are spaced is less transverse to the axis of the conduit 4, the above advantages of spacing the electrodes transversely to the axis of the conduit are achieved to a lesser extent.

Both the embodiments of the selector-detector assembly shown in FIGS. 5 and 6 and in FIGS. 11 and 12 are preferably sterilized after assembly and filled with selective medium shortly before being used. After filling of the dialysis fibre 124, barriers 44 can for example be obtained by clamping the fibre 124 or by sealing the ends of the fibre 124 off using a suitable resin or the like. To replace selective material in the chamber 20, the barriers 44 may be removed temporarily.

Figure 13:
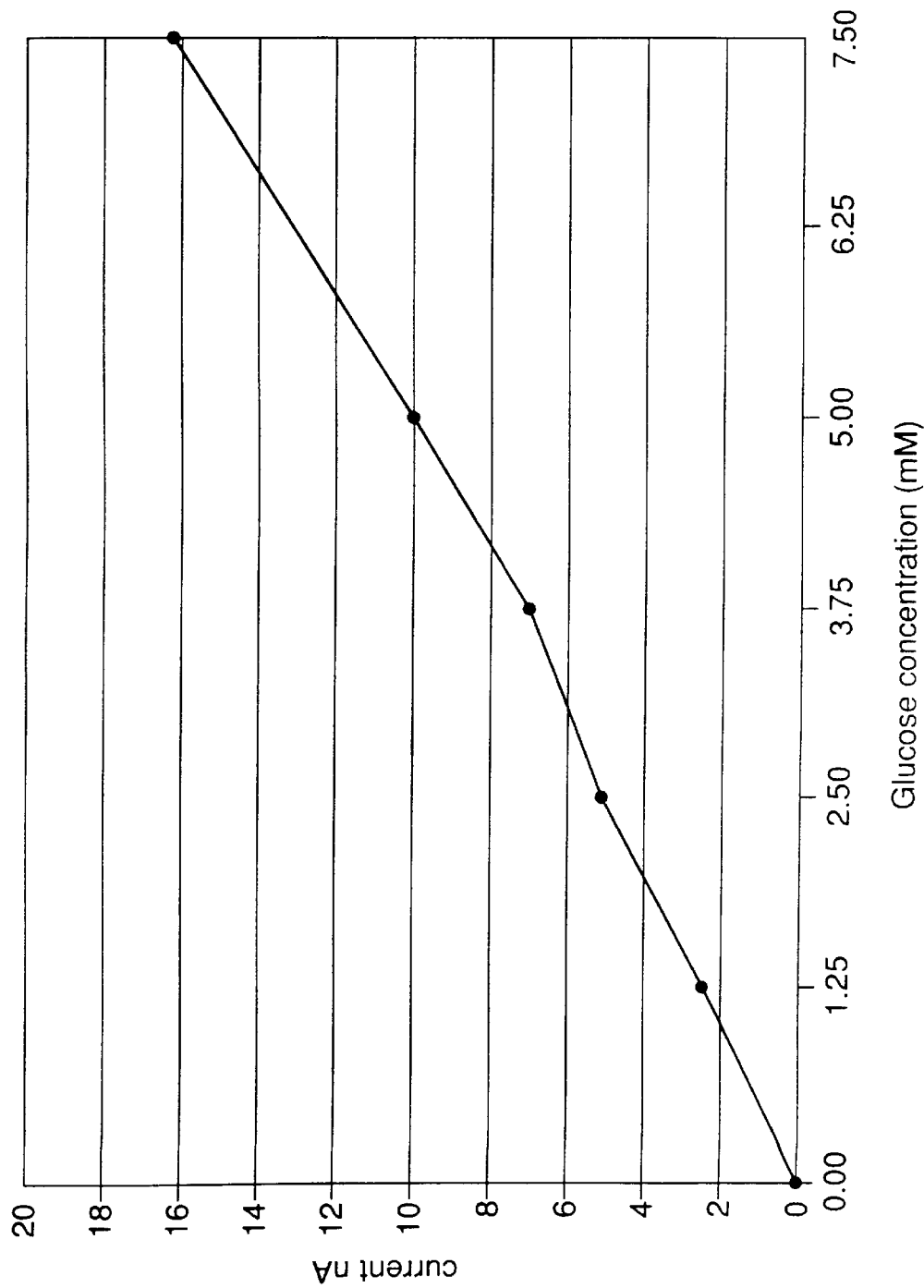
FIG. 13 is a graph showing experimental results obtained with a detection module as shown in FIGS. 11 and 12.

FIG. 13 shows experimental results with a structure as shown in FIGS. 11 and 12 at a flow rate of 6 $\mu$l/hour and glucose oxidase enzymes as selective medium. As can be seen in FIG. 13, already in an experimental set-up a very good linear behaviour of the detector is obtained.

Figure 8:
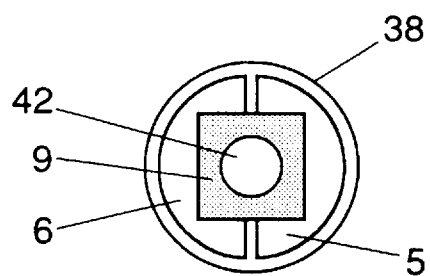
FIG. 8 is a top plan view in cross-section of another device according to the present invention in which a detection module according to FIG. 6 is incorporated.
Figure 9:
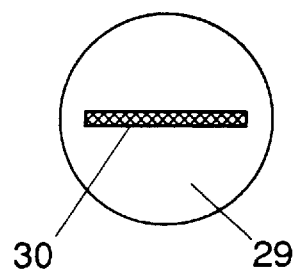
FIG. 9 is a bottom view of the device according to FIG. 8.
Figure 10:
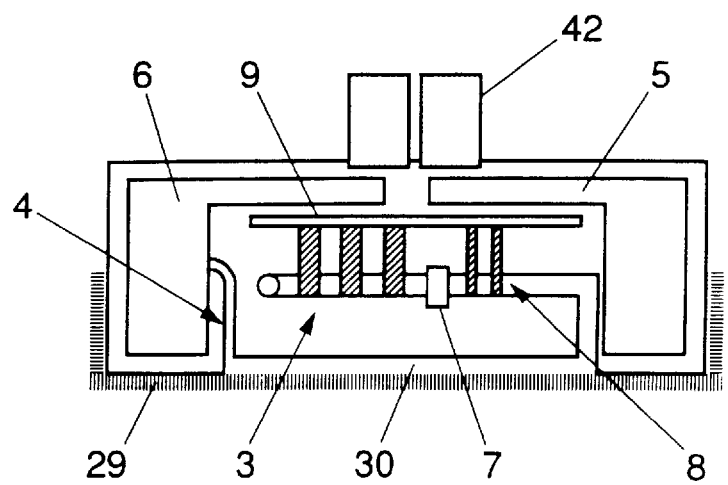
FIG. 10 is a side view in cross-section of the device according to FIGS. 8 and 9.

The general lay-out of the most preferred embodiment of the device according to the invention is shown in FIGS. 8, 9 and 10. The device comprises a generally disk-shaped housing 38 having the size of a wrist-watch. A connector 42 to which an energy supply, a display and registration means can be connected is centrally positioned at one side of the housing 38. Electronics 9 are positioned centrally in the housing 38, between a detector 3, a selector 7, and a preoxidator 8 on one side and the connector 42 on the other side.

The device comprises a supply reservoir 6, a waste reservoir 5 filled with fluid absorbing material, a conduit 4 extending between the supply reservoir 6 and the waste reservoir 5 and an interface in the form of a membrane 29 behind which a portion 30 of the conduit extends. The membrane 29 is to be placed against the skin, substances in the body of the patient pass through the membrane 29, into the part 30 of the conduit 4 behind the membrane 29 and are entrained by passing perfusion fluid. After passing the part 30 of the conduit 4 behind the membrane 29, the perfusion fluid is treated by the preoxidator 8, passed through the selector 7 and a monitoring signal depending on the flux of a substance coming from the selector 7 is generated by the detector 3. The monitoring signal is processed by the electronics 9 and a corresponding signal, which may be a concentration signal representing the concentration in the body fluid of the substance or group of substances to be monitored, is transmitted via the connector 42, where it is used for monitoring and registering the concentration of the selected substance in the body fluid of the patient.

The monitoring signal or the concentration signal can be compared with one or more reference signals to generate control signals if one of the reference signals is reached or passed. The control signals can in turn be used for initiating corrective actions, such as controlling the metering of a medicament and/or triggering an alarm signal for an observing person. Furthermore, a value in accordance with the concentration signal can be displayed and/or registered.

The monitoring signals or the concentration signals can be communicated to and processed at a central processing centre remote from the human or animal body, so that—for instance at night—a single person can watch over the condition of a number of patients.

We claim:

1. A method for monitoring a concentration of a selected substance or of a group of substances in a body fluid of a living human or animal body in wearable device worn on the living human or animal body and comprising an interface to the body, the method comprising the steps of:

holding the wearable device to the body;

transferring the selected substance or group of substances to be monitored from the body through the interface;

transporting the substance or group of substances to be monitored away from behind the interface in a perfusion fluid flow having a flow rate of less than 60 $\mu$l/hour; and measuring the concentration of the substance or group of substances to be monitored in the perfusion flow in the wearable device downstream from the interface.

2. A method according to claim 1 in which said flow rate is less than 20 $\mu$l/hour.

3. A method according to claim 1 in which the flow rate of the perfusion fluid flow is such that a near equilibrium is reached in which the concentrations of the substance or group of substances to be monitored in the body fluid and in the perfusion fluid are substantially identical.

4. A method according to claim 1 in which said measurement comprises the steps of:

selecting the substance or group of substances to be monitored from the perfusion fluid flow in a first location (7); and detecting a concentration in the perfusion fluid flow in a second location (3) downstream from said first location.

5. A method according to claim 4 in which the perfusion fluid is preoxidized in a third location (8) upstream from said first location (7).

6. A method according to claim 4 in which said selecting step comprises the steps of:

providing enzymes selected to catalyse a specified reaction in which the substance or group of substances to be monitored takes part;

immobilizing the enzymes in said first location (7); and passing the perfusion fluid along the enzymes in such a manner that the specified reaction occurs;

the concentration in the perfusion fluid flow detected in said second location (3) being the concentration of a reaction product of said specified reaction.

7. A method according to claim 6 in which input to said specified reaction comprises a reactant dissolved in the perfusion fluid other than the substance or group of substances to be monitored, in which a known fraction of the or each substance to be monitored passes the enzymes without reacting, and in which a remainder of said reactant passes the enzymes without reacting.

8. A method according to claim 7 in which said reactant diffuses more rapidly through the perfusion fluid than the substance or group of substances to be monitored and a fraction of the perfusion fluid is passed through a clearance extending along a porous boundary immobilizing the enzymes.

9. A method according to claim 1 in which the interface (2) is maintained in a subcutaneous position.

10. A method according to claim 1 in which the interface (2) is maintained in an intravascular position.

11. A method according to claim 1 in which body fluid transferred through the interface (2) forms the perfusion fluid.

12. A method according to claim 1 in which the body fluid is dialysed during the transfer through the interface (2).

13. A method according to claim 1, comprising the steps of:

generating a monitoring signal dependent on the concentration of the substance or group of substances to be monitored in said perfusion fluid flow;

comparing said monitoring signal with at least one reference signal; and generating a control signal if said monitoring signal passes beyond said reference signal.

14. A method according to claim 13 in which at least one monitoring or concentration signal is communicated to and processed at a central processing centre remote from the human or animal body, said processing including at least one of the following actions:

calculating a concentration signal representing the concentration in the body fluid of the substance or group of substances to be monitored from said monitoring signal;

displaying a value in accordance with said concentration signal;

comparing said monitoring or concentration signal with at least one reference signal; and generating a control signal if said monitoring or concentration signal passes beyond said reference signal.

15. A method according to claim 1 comprising the steps of:

generating a monitoring signal dependent on the concentration of the substance or group of substances to be monitored in said perfusion fluid flow;

calculating a concentration signal representing the concentration in the body fluid of the substance or group of substances to be monitored from said monitoring signal;

displaying a value in accordance with said concentration signal;

comparing said concentration signal with at least one reference signal; and generating a control signal if said monitoring signal passes beyond said reference signal.

16. A method of monitoring the concentration of a selected substance or group of substances in a body fluid of a living human or animal body in a wearable device, in which the substance or group of substances to be monitored is transferred from the body through an interface and is transported in the wearable device away from behind the interface in a perfusion fluid flow having a flow rate of less than 25 $\mu$l/hour, and in which the concentration of the substance or group of substances to be monitored in the perfusion flow is measured in the wearable device downstream from the interface.

17. A method for monitoring the concentration of a selected substance or group of substances in a body fluid of a living human or animal body, in which the substance or group of substances to be monitored is transferred from the body through an interface and is transported away from behind the interface in a perfusion fluid flow having a flow rate of less than 60 $\mu$l/hour and in which the concentration of the substance or group of substances to be monitored in the perfusion flow is measured downstream from the interface the method comprising the steps of:

selecting the substance or group of substances to be monitored from the perfusion fluid flow in a first location; and detecting a concentration in the perfusion fluid flow in a second location downstream from the first location;

the selecting step comprising the steps of:

providing a complex of antibodies and an antibody-specific detectable derivative of the substance of group of substances to be monitored;

immobilizing the complex in said first location; and passing the perfusion fluid along the complex such that some of the derivative is substituted by the substance or group of substances to be monitored;

the concentration in the perfusion fluid detected in said second location being the concentration of the derivative substituted by the substance or group of substances to be monitored.

18. A method for monitoring the concentration of a selected substance or group of substances in a body fluid of a living human or animal body, in which the substance or group of substances to be monitored is transferred from the body through an interface and is transported away from behind the interface in a perfusion fluid flow having a flow rate of less than 60 $\mu$l/hour, and in which the concentration of the substance or group of substances to be monitored in the perfusion flow is measured downstream from the interface, wherein the method is carried out in situ on the body, the temperature of the perfusion fluid is constant and the perfusion fluid thermally insulated from the environment of the body.

19. A wearable device for monitoring a concentration of a substance or a group of substances in a body fluid of a living human or animal body while the wearable device is worn on the living human or animal body, the wearable device comprising:

a mounting device for mounting the wearable device to the body;

an interface for interfacing the wearable device with the living human or animal body;

a flow channel extending from the interface;

a detector connected in the flow channel; and a flow maintaining device for maintaining a perfusion fluid flow in the flow channel along the interface and the detector at a rate of less than 60 $\mu$l/hour.

20. A device according to claim 19, comprising a selector (7), operatively connected between the interface (2) and the detector (3), in which a substance is immobilized.

21. A device according to claim 20, comprising a preoxidator (8) operatively connected between the interface (2) and the selector (7).

22. A device according to claim 20, wherein the selector (7) comprises means for immobilizing enzymes or a complex of antibodies and an antibody-specific derivative of the substance or group of substances to be monitored.

23. A device according to claim 22, wherein the immobilizing means comprise a chamber (20) with an at least partly porous wall.

24. A device according to claim 23, comprising a clearance space between the chamber and a wall forming a passage along said chamber (20), at least a part of said porous wall bounding said clearance space from said chamber (20).

25. A device according to claim 22 comprising enzymes or a complex of antibodies and an antibody-specific derivative of the substance or group of substances to be monitored immobilized in the selector (7).

26. A device according to claim 19, wherein the interface (2) is formed by a microdialysis tube adapted to be inserted subcutaneously or intravascularly.

27. A device according to claim 19, comprising a catheter in which at least the interface and the detector are positioned.

28. A device according to claim 19, comprising means for calculating a concentration value representing the concentration of the substance or group of substances to be monitored in the body fluid from a monitoring signal dependent on a concentration in the perfusion fluid flow, means for comparing said value with a reference value, means for generating a control signal operatively connected with said comparing means for generating the control signal if the concentration value reaches or passes beyond the reference value, and a user interface for presenting said concentration value to an observing person.

29. A device according to claim 19 wherein the flow maintaining device comprises a fluid absorbing structure.

30. A device according to claim 19 wherein the flow maintaining device comprises a capillary reservoir.

31. A device according to claim 19 wherein the flow maintaining device comprises an osmotic membrane.

32. A device according to claim 19 wherein the flow maintaining device comprises a pressure differential reservoir.

33. A wearable device for monitoring a concentration of substances in a body fluid of a living human or animal body, the device comprising:
   an interface;
   a detector;
   a flow maintaining device for maintaining a perfusion fluid from the interface to the detector at a rate of less than 60 µl/hour;
   a conduit extending between the interface and the detector; and
   a selector operatively connected between the interface and the detector, the selector comprising a chamber formed by a porous tube extending in the conduit, for immobilizing enzymes or a complex of antibodies and an antibody-specific derivative of the substance of group of substances to be monitored.

34. A device according to claim 33 in which the porous tube (124) extends transversely through the conduit (4).

35. A device according to claim 33 in which material in the porous tube (124) is axially displaceable over a predetermined distance.

36. A wearable device for monitoring a concentration of a substance in a body fluid of a living human or animal body, the device comprising:
   an interface;
   a detector;
   a flow maintaining device for maintaining a perfusion fluid from the interface to the detector at a rate of less than 60 µl/hour;
   a selector operatively connected between the interface and the detector, the selector comprising a chamber and a means for immobilizing enzymes or a complex of antibodies and an antibody-specific derivative of the substance of group of substances to be monitored; and
   a barrier for closing off the selector after the chamber is filled.

37. A wearable device for monitoring a concentration of a substance in a body fluid of a living human or animal body, the device comprising:
   an interface;
   an electromechanical amperometric detector comprising a conduit bounded by walls of electrically insulating material, wire shaped electrodes each having a diameter substantially smaller than the diameter of the conduit, extending within the conduit from a wall of the conduit and mutually spaced, at least on the ends of each electrode extending to the outside of the conduit wall;
   flow maintaining device for maintaining a perfusion fluid from the interface to the detector at a rate of less than 60 µl/hour.

38. A device according to claim 37, wherein at least two of the electrodes are cooperating operation electrodes (21, 22) arranged mutually spaced in a direction transverse to the conduit (4).

39. A device according to claim 33, wherein the porous tube comprises a dialysis fibre.

40. A wearable device for monitoring a concentration of a substance in a body fluid of a living human or animal body, the device comprising:
   an interface;
   a detector;
   a flow maintaining device for maintaining a perfusion fluid from the interface to the detector at a rate of less than 60 µl/hour; and
   means for keeping the device in an in situ position on the body; and
   means for controlling the temperature of the perfusion fluid, including a thermally insulating layer covering at least one side of the device and leaving free a side of the device which is to be worn in a position facing the body.

41. A wearable device for collecting a substance or a group of substances in a body fluid of the living human or animal body, the wearable device comprising:
   a mounting unit for mounting the wearable device to the body;
   an interface for interfacing the wearable device with the living human or animal body;
   a collecting reservoir; and
   a flow maintaining device comprising a pressure differential reservoir for maintaining a perfusion fluid flow from the interface to the collecting reservoir at a rate of less than 60 µl/hour.

42. A method for monitoring concentration of a substance or of a group of substances in a body fluid of a living human or animal body, the method comprising the steps of:
- transferring the selected substance or group of substances to be monitored from the body through an interface;
- transporting the substance or group of substances to be monitored away from behind the interface in a perfusion fluid flow;
- providing an immobilized complex of antibodies and an antibody specific detectable derivative of the substance or group of substances to be monitored in the perfusion fluid flow at a first location;
- passing the perfusion fluid along the complex such that some of the derivative is substituted by the substance or group of substances to be monitored; and
- detecting a concentration of the substance or group of substances to be monitored in a second location downstream from the first location;
- wherein concentration in the perfusion fluid detected in the second location is the concentration of the derivative substituted by the substance or group of substances to be monitored.

43. A wearable device for monitoring the concentration of a substance or a group of substances in a body fluid of living human or animal body, comprising:
- an interface;
- a detector communicating with the interface;
- a fluid transfer device for transferring a perfusion fluid from the interface to the detector; and
- a selector operatively connected between the interface and the detector, the selector comprising enzymes or a complex of antibodies and an antibody-specific derivative of the substance or group of substances to be monitored immobilized in the selector.

44. A method for monitoring a concentration of a selected substance or group of substances in a body fluid of a living human or animal body in a wearable device worn on the living human or animal body and comprising a mounting device for mounting the wearable device to the human or animal body, a detector and an interface to the body, the method comprising the steps of:
- mounting the wearable device to the body;
- holding the wearable device against the body;
- transferring the selected substance or group of substances to be monitored from the body through the interface;
- transporting the selected substance or group of substances to be monitored in the wearable device away from behind the interface and along the detector in a perfusion fluid having a flow rate of less than 60 µl/hour; and
- measuring the concentration of the substance or group of substances to be monitored in the perfusion flow in the detector downstream from the interface.

45. A method for monitoring a concentration of a selected substance or group of substances in a body fluid of a living human or animal body in a wearable device while worn on the living human or animal body and comprising an interface to the body, the method comprising the steps of:
- transferring the selected substance or group of substances to be monitored from the body through the interface;
- transporting the selected substance or group of substances to be monitored in the wearable device away from the from behind the interface by a non-moving means in a perfusion fluid having a flow rate of less than 60 µl/hour by a non-moving means; and
- measuring the concentration of the substance or group of substances to be monitored in the perfusion flow in the wearable device downstream from the interface.

46. A wearable device for monitoring a concentration of a substance or a group of substances in a body fluid of living human or animal body while the wearable device is worn on the living human or animal body, the wearable device comprising:
- an interface for interfacing the device with the living human or animal body and comprising a window adapted to be held against an outer skin of the living human or animal body;
- a detector connected to the interface; and
- a flow maintaining device for maintaining a perfusion fluid flow from the interface to the detector at a rate of less than 60 µl/hour.

47. A wearable device for monitoring a concentration of a substance or a group of substances in a body fluid of living human or animal body while the wearable device is worn on the living human or animal body, the wearable device comprising:
- an interface for interfacing the device with the living human or animal body;
- a detector connected to the interface; and
- a fluid flow maintaining means, which in operative condition is a non-moving device, for maintaining a perfusion fluid flow from the interface to the detector at a rate of less than 60 µl/hour.

48. A device according to claim 19, comprising means for calculating a concentration value representing the concentration of the substance or group of substances to be monitored in the body fluid from a monitoring signal dependent on a concentration in the perfusion fluid flow, means for comparing said value with a reference value, means for generating a control signal operatively connected with said comparing means for generating the control signal if the concentration value reaches or passes beyond the reference value, and a user interface for presenting said concentration value to an observing person.

49. A method of monitoring the concentration of a selected substance or group of substances in a body fluid of a living human or animal body, in which the substance or group of substances to be monitored is transferred from the body through an interface and is transported away from behind the interface and along a detector in a perfusion fluid flow having a flow rate of less than 59 µl/hour, and in which the concentration of the substance or group of substances to be monitored in the perfusion flow is measured by the detector downstream from the interface.

50. The method in accordance with claim 49 wherein the flow rate is less than 40 µl/hour.

51. A method of monitoring the concentration of a selected substance or group of substances in a body fluid of a living human or animal body, in which the substance or group of substances to be monitored is transferred from the body through an interface and is transported away from behind the interface and along a detector in a perfusion fluid flow having a flow rate of less than 0.99 µl/minute, and in which the concentration of the substance or group of substances to be monitored in the perfusion flow is measured by the detector downstream from the interface.

52. A wearable device for monitoring a concentration of a substance or a group of substances in a body fluid of living human or animal body, comprising:

an interface;

a detector for measuring the concentration of substances in a fluid flow flowing along the detector; and a flow maintaining device for maintaining a perfusion fluid flow from the interface and along the detector at a rate of less than 59 µl/hour.

53. The wearable device in accordance with claim 52 the flow maintaining device maintains the fluid flow from the interface to the detector ata rate of less than 40 µl/hour.

54. A wearable device for monitoring a concentration of a substance or a group of substances in a body fluid of living human or animal body, comprising:

an interface;

a detector for measuring the concentration of substances in a fluid flow flowing along the detector; and a flow maintaining device for maintaining a perfusion fluid flow from the interface and along the detector at a rate of less than one µl/minute.

* * * * *

UNITED STATES PATENT AND TRADEMARK OFFICE
CERTIFICATE OF CORRECTION

PATENT NO. : 6,013,029
DATED : 01/11/00
INVENTOR(S) : KORF, JACOB, et al.

It is certified that error appears in the above-identified patent and that said Letters Patent is hereby corrected as shown below:

Col. 18, line 20:
    after "hour" insert --,--
Col. 20, line 31:
    before "flow" insert --a--
Col. 22, lines 31-41:
    please delete entire claim 48 and substitute therefor:
    48. A device according to claim 47, wherein the means for maintaining a flow comprise driving means located downstream of the detector, said driving means being adapted for drawing perfusate from the interface to the detector, and a restriction for controlling the flow rate, wherein said restriction is located between the detector and said driving means.

Signed and Sealed this

Ninth Day of January, 2001

Attest:

Attesting Officer

Q. TODD DICKINSON
Commissioner of Patents and Trademarks